US012637419B2

(12) United States Patent
Stavrou et al.

(10) Patent No.: US 12,637,419 B2
(45) Date of Patent: May 26, 2026

(54) RECOVERY OF WATER-FREE METHANESULFONIC ACID FROM THE BOTTOM STREAM OF A DISTILLATION COLUMN

(71) Applicant: BASF SE, Ludwigshafen am Rhein (DE)

(72) Inventors: Marina-Eleni Stavrou, Ludwigshafen (DE); Marcus Bechtel, Ludwigshafen (DE); Rosario Mazarro Berdonces, Ludwigshafen (DE); Frank Piepenbreier, Ludwigshafen (DE); Chee Jian Chan, Ludwigshafen (DE); Bjoern Kaibel, Ludwigshafen (DE); Andreas Kempter, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 1048 days.

(21) Appl. No.: 17/633,058

(22) PCT Filed: Jul. 28, 2020

(86) PCT No.: PCT/EP2020/071271
§ 371 (c)(1),
(2) Date: Feb. 4, 2022

(87) PCT Pub. No.: WO2021/023582
PCT Pub. Date: Feb. 11, 2021

(65) Prior Publication Data
US 2022/0274919 A1 Sep. 1, 2022

(30) Foreign Application Priority Data
Aug. 7, 2019 (EP) .................................... 19190621

(51) Int. Cl.
*C07C 303/06* (2006.01)
*C07C 303/44* (2006.01)

(52) U.S. Cl.
CPC .......... *C07C 303/06* (2013.01); *C07C 303/44* (2013.01)

(58) Field of Classification Search
CPC ........................... C07C 303/44; C07C 303/06
See application file for complete search history.

(56) References Cited

U.S. PATENT DOCUMENTS

| | | | | | |
|---|---|---|---|---|---|
| 4,035,242 A | * | 7/1977 | Brandt | ................. | C07C 143/02 |
| | | | | | 203/15 |
| 4,450,047 A | * | 5/1984 | Malzahn | ................. | B01D 3/10 |
| | | | | | 203/15 |

(Continued)

FOREIGN PATENT DOCUMENTS

| | | |
|---|---|---|
| CN | 108463455 A | 8/2018 |
| DE | 2045087 A1 | 3/1971 |

(Continued)

OTHER PUBLICATIONS

Practical Process & Research Development, 5th Ed., 2000, pp. 27-52 (Anderson).*

(Continued)

*Primary Examiner* — Amy C Bonaparte
*Assistant Examiner* — Derek Rhoades
(74) *Attorney, Agent, or Firm* — ArentFox Schiff LLP

(57) ABSTRACT

Process for separating anhydrous methanesulfonic acid from a reaction mixture comprising methanesulfonic acid and sulfuric acid by distillation with at least three functional steps and the use of said methanesulfonic acid.

15 Claims, 3 Drawing Sheets

Type 1-1

Type 1-2

(56) References Cited

U.S. PATENT DOCUMENTS

| | | | |
|---|---|---|---|
| 4,938,846 | A | 7/1990 | Comstock et al. |
| 2010/0087674 | A1 | 4/2010 | Reinhardt et al. |

FOREIGN PATENT DOCUMENTS

| | | | | |
|---|---|---|---|---|
| DE | 3921130 | A1 | 1/1991 | |
| GB | 1350328 | A | 4/1974 | |
| KR | 20180081577 | A | 7/2018 | |
| WO | 0031027 | A1 | 6/2000 | |
| WO | 2015071365 | A1 | 5/2015 | |
| WO | WO 2015/071455 | A1 * | 5/2015 | ........... C07C 309/00 |
| WO | WO 2018/208701 | A1 * | 11/2018 | .............. B01D 3/10 |
| WO | 2018219726 | A1 | 12/2018 | |
| WO | 2021023583 | A1 | 12/2021 | |

OTHER PUBLICATIONS

Vogel's Textbook of Practical Organic Chemistry, 5th Ed. (1989) (Vogel).*

Diaz-Urrutia, et al., "Activation of methane: A selective industrial route to methanesulfonic acid", Science, vol. 363, Issue 6433, Mar. 22, 2019, pp. 1326-1329.

European Search Report for EP Patent Application No. 19190621.3, Issued on Jan. 30, 2020, 3 pages.

International Search Report for PCT Patent Application No. PCT/EP2020/071271, Issued on Oct. 5, 2020, 3 pages.

Kappenthuler, et al., "Environmental assessment of alternative methanesulfonic acid production using direct activation of methane", Journal of Cleaner Production, vol. 202, Nov. 20, 2018, pp. 1179-1191.

* cited by examiner

5

20

Type C1-1

Type C1-2

Type C1-3

Type C2

30

5

10

15

RECOVERY OF WATER-FREE METHANESULFONIC ACID FROM THE BOTTOM STREAM OF A DISTILLATION COLUMN

CROSS-REFERENCE TO RELATED APPLICATIONS

This application is a National Stage Entry of PCT/EP2020/071271, filed Jul. 28, 2020, which claims priority to EP application Ser. No. 19190621.3, filed Aug. 7, 2019, the disclosures of each of which are hereby incorporated by reference in their entirety.

The present invention relates to a process for the separation of water-free methanesulfonic acid from a reaction mixture obtained by the synthesis of methanesulfonic acid.

Methanesulfonic acid ("MSA"), like other alkanesulfonic acid, is a strong organic acid with a large range of applications. MSA is used e.g. in the galvano industry, in chemical synthesis, in cleaning applications, in the biodiesel industry and many other applications.

DE 3921130 describes a process in which alkane sulfonic acids are produced from their alkali salts in a reaction with HCl. The formed salts are precipitating and removed via filtration or centrifugation. Alkane sulfonic acids are recovered from the liquid phase by a two-step distillation. Remaining HCl is removed in the first step and an azeotropic mixture of HCl/water is withdrawn in the second step. The distillation is performed at low vacuum and temperatures below 100° C. The aqueous alkane sulfonic acid is obtained as a bottom product with a water content of 1 to 30 wt.-%, preferably 10 to 20 wt.-%. There are no other impurities mentioned in the feed to distillation. Thus, the distillation task is very simple due to the low complexity of the feed to the distillation and the wide gap in boiling points between HCl, H₂O and MSA.

WO 2000/31027 claims the production of methane sulfonic acid via the oxidation of dimethyl disulfide with nitric acid. In this reaction nitrogen oxides are formed which are again converted with oxygen to nitric acid. The aim of purification is to produce anhydrous methane sulfonic in a distillation process. In a first column, large fractions of water and low boiling nitric acid are removed at low vacuum. Then the bottom product of the first column, containing 1 wt.-% of water and 1 wt.-% of sulfuric acid is further purified in a second column operated under high vacuum. From this column methane sulfonic acid is withdrawn at a side discharge with a purity higher than 99.5 wt.-% and low sulfuric acid concentrations below 50 ppm. The distillation task is of moderate complexity since there are many compounds boiling at lower temperatures than MSA ("light boilers", "lights", "light boiling components") in the feed to the distillation (wide gap in boiling points to MSA) and only a small amount of so-called high boilers, i.e. compounds boiling at higher temperatures than MSA, such as sulfuric acid.

GB 1350328 describes a process for the production of alkanesulfonic acids from alkyl mercaptans or dialkyldisulfides in aqueous HCl via chlorination. This reaction delivers aqueous alkane sulfonic acid with a water content of 15 to 30 wt.-% and traces of high boilers like sulfuric acid. To obtain a refined alkane sulfonic, first water is boiled off and then the product alkane sulfonic acid is distilled and recovered as the top product. The distillation has similar characteristics as described for WO 2000/31027.

U.S. Pat. No. 4,035,242 discloses the purification of alkanesulfonic acid from an aqueous solution with a water content of 10 wt.-% or higher. In a two-step distillation process, alkane sulfonic acids with a water content of 2 wt.-% or less are obtained. This patent mentions the formation of methyl methanesulfonate ("MMS") due to the operation of the distillation at high temperatures. In the first distillation step a large fraction of water is withdrawn as a low boiler at reduced pressure between 130 and 670 mbar and a temperature of 171 to 186° C. The second distillation column is operated at further reduced pressure of 1 to 80 mbar and temperatures of 188 to 205° C. In this step methanesulfonic acid is separated from light boilers including water and MMS and "heavy boilers" like sulfuric acid (in general, the term includes compounds with a boiling point higher than MSA at the given conditions, equivalent terms are "heavies", "high boilers" or "high boiling components"). The product alkane sulfonic acid is withdrawn from the second column at a side discharge above the feed point. The distillation has similar characteristics as described for WO 2000/31027.

U.S. Pat. No. 4,450,047 claims the removal of water from an aqueous methanesulfonic acid solution with a water content of 5 to 60 wt.-% with a falling film evaporator at reduced pressure. A purity of 99.5 wt.-% is reached and the MMS concentration is reported to be below 1 ppm.

U.S. Pat. No. 4,035,242 describes the evaporation of water from an aqueous solution with the help of two falling-film evaporators operating in series at reduced pressure.

In both US patents the set-up with a falling film evaporator is well suitable to remove the light boiler water while at the same reducing the residence time of the product stream in the distillation. In this way the formation of MMS can be kept to a minimum. However, separation of MSA from potential high boilers cannot be achieved in this set-up.

WO 2015/071365 discloses a process for the synthesis of alkanesulfonic acids from SO₃ and an alkane with the help of a dialkylsulfonyl peroxide. It is mentioned that the reaction product may further be processed by distillation, but no details are given.

WO 2015/071455 describes a process in which an alkanesulfonic acid is formed from SO₃ and an alkane with help of an alkylsulfonylperoxide as a radical starter. The reaction is performed with MSA and oleum/sulfuric acid as solvent. Furthermore, the separation of the reaction products by means of distillation is described. However, no detailed information about the distillation set-up and the conditions are given, in particular the amount of side products, such as high boilers like sulfuric acid, remaining in the final product, i.e. MSA, are not mentioned. It is described that the bottom product of the distillation contains H₂SO₄ and up to 10 wt.-% alkanesulfonic acid. The bottom product is recycled to the reaction part and can be used e.g. for the formation of the radical starter.

WO2018/208701 aims at the recovery of purified MSA after it was formed in a radical reaction from methane and SO₃. The patent claims the processing of unconverted SO₃ with preferably water to form a heavy boiling compound like sulfuric acid under pressure. Some details about the column internals and the operating pressure are given. However, the patent contains no information about the separation of MSA from water, which was previously added in excess.

Diaz-Urrutia and Ott, *Science,* 2019, 363, pp 1326-1329 report the operation of a pilot plant for the production of MSA from SO₃ and methane with the help of an electrophilic initiator. The reaction is carried out in a cascade of reactors under pressure. After depressurization the unconverted SO₃ is quenched with water in a glass reactor. The mixture after the quench step contains $MSA/H_2SO_4$ in a ratio of about 40:60 and is transferred to a vacuum distillation column. The column is operated at a pressure of 10 mbar and a max. temperature of 220° C. The authors state, that MSA with a purity of 99.9% is recovered as the distillate at the head of the column while a mixture of $MSA/H_2SO_4$ as a bottom product is recycled to the reactor cascade. Furthermore, a yield of about 80% is claimed to be the optimum of the process. No detailed information is provided on the distillation, neither regarding the set-up (e.g. number of theoretical stages, F-factor) nor the composition of the feed to distillation, especially if there were any impurities or side products from the synthesis step.

Kappenthuler et al. [*Journal of Cleaner Production*, 202, 2018] evaluates the ecological impact of the production of MSA from $SO_3$ and methane compared to the oxidation of dimethyl disulfide. In the methane-based process a mixture of MSA, sulfuric acid and leftover of water is fed to a distillation column. The distillation conditions are 200° C. and 10 mbar (assumed based on the physical properties). MSA with a purity of 99.5 wt.-% is obtained as distillate and the bottom product consists of 80:20 mixture of MSA and sulfuric acid. No detailed information is provided on the distillation, neither regarding the set-up (e.g. number of theoretical stages, F-factor) nor the composition of the feed to distillation, especially if there were any impurities or side products from the synthesis step.

WO2018/219726 claims a distillation concept for the production of water-free MSA with at least two distillation columns, wherein the feed comprises MSA, sulfuric acid, methanesulfonic acid anhydride, MMS and traces of sulfur trioxide. Due to the presence of high boilers in the feed to the distillation, in all set-ups the product MSA is withdrawn at a side discharge. The formation of decomposition products of MSA like MMS and others in the distillation bottom due to high temperatures is described.

In the light of the prior art the technical problem underlying the present invention was the provision of a process for separating methane sulfonic acid, MSA, obtained from reaction mixtures, that overcomes the disadvantages of those processes known in the art. In particular, a process was to be provided which has an improved energy demand, in particular compared to processes where MSA is delivered as a liquid side-discharge. Furthermore, a process should be provided which allows a variation of the feed with regard to side-products such as sulfuric acid, $SO_3$ or MMS and which also could handle generation of side-products due to thermal degradation during the separation process itself, leading to the desired product specifications.

The problem is solved by the features of the independent claims. Preferred embodiments of the present invention are provided by the dependent claims.

The invention relates to a process for separating anhydrous methanesulfonic acid from a reaction mixture comprising methanesulfonic acid and sulfuric acid by distillation with at least three functional steps, characterized that in the first functional step the reaction mixture is fed into a first column K1, where the top stream of column K1 is then transferred to the second functional step, wherein this second functional step is a second column K2, in which purified anhydrous methanesulfonic acid is obtained from its bottom stream, and wherein the bottom stream of column K1 is transferred to a third functional step, wherein this third functional step is either a third column K3 or an evaporator W3-1, in which the top stream is recycled back into column K1, and in which the bottom stream is separated from the distillation process.

The term "anhydrous methanesulfonic acid" in this inventive process refers to an anhydrous MSA quality as commonly available on the market, i.e. it may still contain traces of water, e.g. less than 0.5 wt-%, or more common less than 0.2 wt-%, less than 0.1 wt-% or less than 0.05 wt-%.

A further preferred embodiment relates to a process, in which in addition to an evaporator W3-1 further (n–1) evaporators W3-2, W3-3, ..., W3-n, n being an integer from 2 to 10, are used in the third functional step, wherein the bottom stream of each evaporator W3-k, k being an integer from 1 to (n–1)) is transferred to each evaporator W3-(k+1), and wherein the top stream of each evaporator W3-(k+1) is transferred back to each evaporator W3-k, while the bottom stream of evaporator W3-n is separated from the distillation process.

Another embodiment relates to a process, in which the third functional distillation step is realized with a combination of a column K3 and one or several evaporators W3-1, W3-2 ... in series.

Another preferred embodiment relates to the inventive process, wherein the reaction mixture comprises 55 to 95 wt.-% methanesulfonic acid, 5 to 45 wt.-% sulfuric acid, 0 to 5 wt.-% methanesulfonic acid anhydride, 0 to 1 wt.-% side products, 0 to 5% $SO_3$, 0 to 5 wt.-% of water and traces of methane, wherein the sum of all components sums up to 100 wt.-%, and wherein the side products comprise methylmethanesulfonate and/or methylbisulfate and/or methanedisulfonic acid, and wherein the amount of components other than methanesulfonic acid and sulfuric acid is in the range of 0 to 10 wt.-%.

A further embodiment relates to the inventive process, wherein the at least two columns K1, K2 and optionally K3 can each be set-up as one column K1 and K2 and optionally K3, or as several columns with same functionalities K1, K2 and optionally K3 operated in parallel.

A further embodiment relates to the inventive process, wherein the bottom residue of column K3 or evaporator or cascade of evaporators W3-n contains at least 60 wt.-% of sulfuric acid.

A further embodiment relates to the inventive process, wherein the pressure at the head of the columns and optionally evaporators ranges from 0.1 to 50 mbar, for all distillation columns K1, K2 and optionally K3 and evaporators W3-n.

A further embodiment relates to the inventive process, wherein the temperature at the bottom of the columns and optionally evaporators ranges from 140 to 220° C., in all distillation columns K1, K2 and optionally K3 and evaporators W3-n.

A further embodiment relates to the inventive process, wherein purified MSA leaves the distillation at bottom of K2 with a specification of <500 ppm sulfuric acid, <1000 ppm MMS, 0.5 wt.-% water.

A further embodiment relates to the inventive process, wherein MSA leaves the distillation with a purity of at least 98 wt.-%.

A further embodiment relates to the inventive process, wherein the process is a batch or a continuous process.

A further embodiment relates to the inventive process, wherein the MSA recovery rate in the distillation is at least 80%.

A further embodiment relates to the inventive process, wherein the energy demand for MSA distillation is less than 800 kW/kg MSA, depending on the concentration of sulfuric acid, in particular if the concentration of sulfuric acid is 25%.

A further embodiment relates to the inventive process, wherein at least a part of the bottom fraction of the MSA distillation column K3 is not purged from the system but at least partially recycled to the synthesis step of the starter solution or to the synthesis step of the MSA synthesis with methane and $SO_3$.

A further embodiment relates to the inventive process, wherein the residence time in each distillation column and optionally evaporators W3-n is below 5 h.

A further embodiment relates to the inventive process, wherein the ratio of the inner column diameter in the sump and the inner column diameter of the column directly above the sump for each column is in the range from 0.20 to 0.99.

It is clear that the described process also can be used to separate or purify other alkanesulfonic acids such as ethanesulfonic acid, n-, i-propanesulfonic acid, n-, i-, sec.- or tert.-butanesulfonic acid or mixtures thereof.

According to the inventive process sulfuric acid and other heavy boiling components are separated from MSA and the light boilers in a first functional step. Light boilers are separated from MSA in a second functional step using a distillation column and the purified MSA is removed from the column as bottom product. In the third functional step the heavy boilers, especially sulfuric acid, are enriched and one fraction of the bottom stream is discarded in a purge stream while the other fraction optionally can be recirculated to the MSA synthesis.

The third functional step leads to a reduction of MSA-product losses and defines the remaining concentration of MSA in the bottom of the second column which corresponds to the MSA concentration in the bottom purge and the recycle stream to the process. The adjustment of the MSA concentration in this stream is also termed "conditioning" of the sulfuric acid rich stream that is directed back to the reaction section. The third separation step is realized using a distillation column. Depending on the capacity of the MSA process each of the columns in the three distillation steps can be realized as one column or more than 1 column with the same function set-up in parallel. Moreover, in the third separation step the distillation can be realized in a simple evaporator or a cascade of evaporators. This alternative realization of the third distillation step may optionally include one expansion vessel per evaporator or on expansion vessel per evaporator cascade. Realization of the third distillation step as column or set of columns operated in parallel is preferred.

In a preferred embodiment the sulfuric acid rich stream leaving the third separation step at the bottom e.g. column K3 contains less than 40 wt.-% MSA, preferably less than 35 wt.-%, and most preferably less than 30 wt.-%, or less than 25 wt.-%, 20 wt.-%, 15 wt.-%, less than 10% or less than 5% MSA.

As a rule, the methanesulfonic acid produced with the inventive process here has a purity of more than 98.0 wt.-%, preferably more than 98.5 wt.-% or 99.0 wt.-%, and most preferably more than 99.2 wt.-%, 99.4 wt.-% or 99.5 wt.-%. If desired, it can be as high as 99.6 wt.-%, 99.7 wt. %, 99.8 wt.-% or 99.9 wt.-%. Usually, the purified MSA contains essentially no water. The term "essentially" refers to the quality "water-free MSA" sold under various trade names on the market which usually means less than 0.5 wt.-% water (assuming that for the water-free MSA with a content of MSA according to the respective specifications of at least 99.5 wt.-% all the delta to 100% is water). In a preferred mode the water content is less than 0.4 wt.-%, or less than 0.3 wt.-%, or less than 0.2 wt.-% or even below 0.1 wt.-% or below 0.05 wt.-%. In general, the sulfuric acid content in the purified MSA is less than 500 ppm or less than 300 ppm or less than 100 ppm, preferred less than 50 ppm and even more preferred less than 30 ppm, 20 ppm or 10 ppm. This value can be given as sulfuric acid or as sulfate concentration, both parameters are considered equivalent in this application. Generally, the content of MMS in the purified MSA is less than 1000 ppm or less than 500 ppm. In a preferred mode the MMS content in the purified MSA is less than 300 ppm and even more preferred less than 200 ppm or less than 150 ppm or less than 100 ppm.

The optimized process for the production and purification of methane sulfonic acid is described in detail in the following and a schematic flow chart of a process set-up can be found in FIG. 1:

1. Reaction: In a reaction step MSA can be formed from methane and $SO_3$ with MSA and sulfuric acid as a solvent under pressure. A peroxide initiator for the reaction may be formed with hydrogen peroxide and a recycle stream from the distillation mainly consisting of MSA and sulfuric acid can be added at this stage. A typical reaction can take place at a pressure in the range of from 50 to 120 bar and at a temperature in the range of from 40 to 70° C. The reaction set-up can consist of one reactor or several reactors in cascade. The reaction mixture leaving the reactor usually comprises from 55 to 95 wt.-% MSA (or higher), 5 to 45 wt.-% $H_2SO_4$, 0 to 5 wt.-% methanesulfonic acid anhydride ("MSAA"), 0 to 1 wt.-% methylmethanesulfonate ("MMS"), 0 to 5 wt.-% $SO_3$ and traces of methane. Further examples to generate MSA from $SO_3$ and methane can be found in the state of the art.

2. Quench: $SO_3$ and/or MSAA can be partially or completely converted with water to $H_2SO_4$ and MSA, respectively, either if the reaction mixture is still under pressure (above ambient pressure) with methane or if the reaction solution is already decompressed (the pressure then being slightly above ambient pressure, at ambient pressure, or below ambient pressure). Water can be added understoichiometrically or stoichiometrically relative to the total amount of $SO_3$ and MSAA. Water can also be added stochiometrically to convert $SO_3$ to sulfuric acid, but still understochiometric with regard to MSAA. However, complete conversion of $SO_3$ and of MSAA prior to distillation by addition of water in stochiometric or even slightly overstochiometric amounts relative to the total amount of $SO_3$ and MSAA are preferred.

3. Decompression: As a rule, when reducing the pressure, a "light stream" consisting mainly of methane and a "heavy stream" consisting mainly of MSA and sulfuric acid is formed. The heavy stream preferably is purified in a distillation step.

4. Distillation: The feed to the distillation, the above heavy stream, typically contains 55 to 95 wt.-% MSA, preferably 60 to 90 wt.-% MSA and more preferably 65 to 85 wt.-% MSA, 5 to 45 wt.-% sulfuric acid, 0 to 1 wt.-% $H_2O$ and 0 to 1 wt.-% or higher further compounds such as for example MMS, methyl bisulfate ("MBS"), or methane disulfonic acid ("MDSA"). If water is added understoichiometrically in the quench, the feed to the distillation usually is water-free, but could contain traces of sulfur trioxide and MSAA. Additionally, in all cases the feed may contain traces of methane. However, due its high volatility, generally methane would readily leave the distillation unit as an inert component.

The feed stream to the distillation can be sent to the distillation at the same temperature as it leaves the quench step or the decompression step, but it could also be preheated prior to entering the distillation set-up, e.g. it can be heated up to a temperature in the range of from 80 to 160° C., preferably from 100 to 160° C., more preferably from 120 to 160° C., but also even higher as 160° C.

The distillation set-up usually comprises three functional steps as shown in FIG. 2. The stream generally coming from the decompression section is fed to column K1 (one functional column or more than one column with identical functionality operated in parallel). In column K1 heavy boilers and low boilers are separated. The stream usually comprising water, light boiling side-products of the reaction, potentially impurities introduced via the raw materials (especially via $SO_3$ and methane), potentially traces of $SO_3$ and methane, and MSA is leaving K1 at the top, while the high boilers leave the column at the bottom. The stream contains MSA, sulfuric acid and other high boilers of the reaction.

The light boiling stream leaving K1 at the top mainly usually consists of MSA and other light boilers like MMS, MBS, $H_2O$, and $CH_4$ and potentially traces of $SO_3$. This stream is fed to a second functional column K2 or a series of columns K2-n with same functionality operated in parallel. As a rule, in this second step light boiling components are separated from the product MSA which leaves the column at the bottom with a purity of 98.0 wt.-% or higher as described above. The product can be withdrawn from the bottom of the column either in liquid form or as a gaseous bottom side discharge.

If the product is withdrawn in liquid form, it can be obtained either directly from the bottom stream or from a liquid collector between the bottom and the packing.

The heavy boiling stream leaving the first distillation at the bottom is fed to the column K3 or several columns K3-n operated in parallel. The target of the separation equipment in this third step is to recover MSA from the sulfuric acid rich stream, namely decrease product losses and increase the overall recovery rate of MSA in the separation. This can be achieved with the help of a distillation column (Type 1-1). In an alternative set-up the column or set of columns is replaced by an evaporator or a cascade of evaporators (Type 1-2). Suitable types of reboilers may be Kettle Type reboilers, thermosyphon reboilers, forced circulation reboilers, thin film evaporators, falling film evaporators, block heat exchangers or tube bundle heat exchangers. Again, if the capacity cannot be handled by one column or evaporator then a set of columns or evaporators having the same function and operating conditions could be set-up in parallel to match equipment design with the plant capacity. The MSA-rich stream is directed back to the bottom of the first distillation column K1 or distillation columns K1-n. The sulfuric acid rich stream could be disposed of or recycled, completely or partially, as described above. It is conditioned to meet a concentration window typically between 5-40 wt.-% MSA.

In general, all distillation columns are operated under reduced pressure in the range of from 0.1 to 50 mbar, preferably 2 to 30 mbar, more preferably 3 to 20 mbar and most preferably 5 to 15 mbar (all values given as absolute pressure at the heads of the columns and evaporators). Both bottom temperatures of the distillation columns and residence times in the bottom section of the distillation (i.e. the volume in the sump of the columns including heat exchangers, pumps, piping etc.) should be kept as low as possible to avoid decomposition of MSA. For this reason, the bottom temperatures are controlled to be typically between 140° C. and 220° C., preferably between 150 and 210° C., more preferably between 160° C. and 200° C. and most preferably between 165 and 195° C. or 170 and 190° C. The distillation columns K1, K2 and K3 might be all operated at the same temperature and pressure or at different temperatures and pressures. If a reboiler or cascade of reboilers in series is used, with or without one joint expansion vessel or individual vessels for each evaporator, instead of a distillation column K3 they are operated at the same conditions as described for column K3. If a cascade of reboilers is used, they might be operated at the same temperature and pressure or at different temperature and pressures. The reboilers of columns K1, K2 and K3 are based on the principle of natural circulation evaporator or a forced circulation evaporator or a forced circulation flash evaporator. Besides this type of reboilers also thermosyphon reboilers, kettle type reboilers, falling film evaporators and thin film evaporators can be used. The distillation set-up can apply different evaporator concepts or the same concept for all columns or set of columns K1, K2 and K3. Typically, the same evaporator concept is applied for all columns. Using a forced circulation evaporator or a forced circulation flash evaporator is preferred.

Condensers can be designed according to the principle of surface condensation or the principle of direct/spray condensation.

All reboilers and evaporators in the distillation set-up can be either heated with steam or a liquid heat transfer fluid. The condensers on top of all distillation columns are cooled with water or another cooling liquid, e.g. a sole, glycols, etc. Cooling with water is preferred. The distillation columns can be evacuated with a jet-pump, a liquid-ring compressor, a membrane compressor, a piston compressor, a roots compressor or combinations of these types of compressor. If needed a condensate trap can be placed before this equipment.

The inventive process enables a robust operation as a product with high purity can be produced over a wide range of parameters as for example variations in the MSA-sulfuric acid ratio, of the feed composition to distillation regarding reaction side-products and impurities, of the pressure, of the temperature etc.). This design enables a robust operation and the recovery of pure MSA in spite of variations in the feed composition, especially regarding changes in the MMS-concentration and the sulfuric acid concentration.

Moreover, the inventive process achieves a high recovery rate of MSA. In addition, it is possible to further reduce product and sulfuric acid losses, if the sulfuric acid rich stream is recycled, partially or completely, e.g. to the reaction section of the process and/or to the synthesis of the starter. The composition of the sulfuric acid rich stream returned to the reaction section is a further specification of the process as it has an impact on the overall energy demand.

The MSA obtained by the inventive process can be used in the known applications. Therefore another embodiment concerns the use of MSA, obtainable by the inventive, for cleaning applications, for chemical synthesis or in an electroplating process.

9

Figure 2:
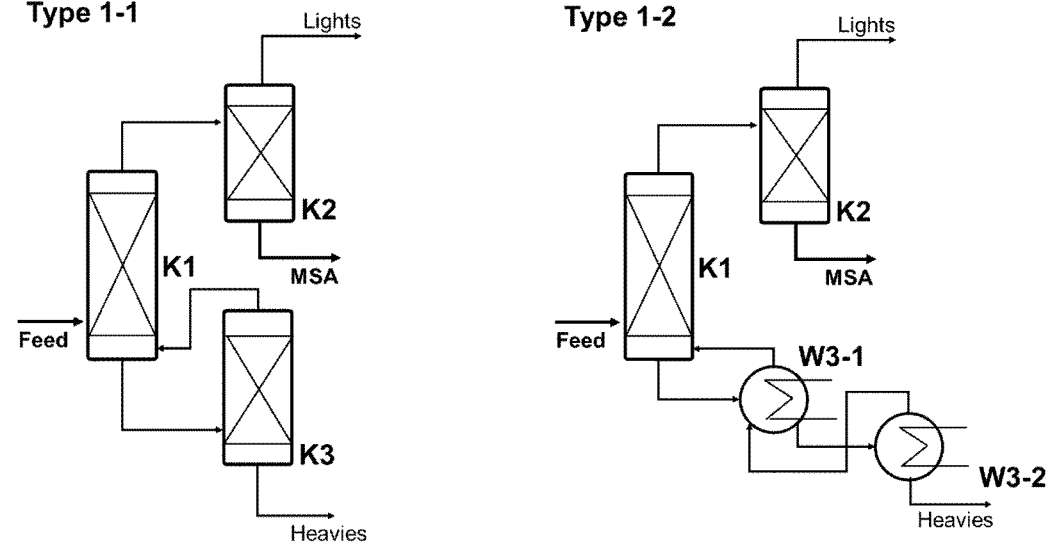

FIG. 2 shows a distillation set up with a distillation column (Type 1-1), and, alternatively, where the column or set of columns is replaced by an evaporator or a cascade of evaporators (Type 1-2).

Figure 3:
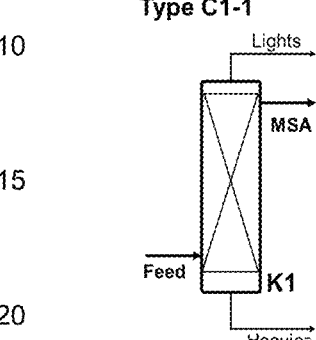
Figure 3:
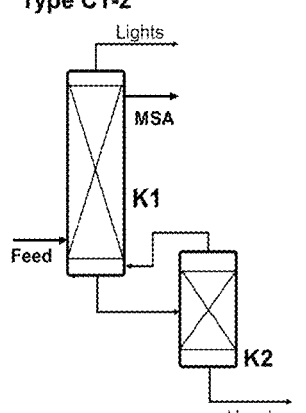
Figure 3:
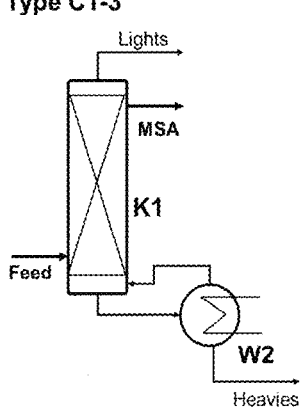

FIG. 3 shows a distillation set up with a single column (Type C1-1), a subsequent distillation column (Type C1-2), and a cascade of evaporators (Type C1-3).

Figure 4:
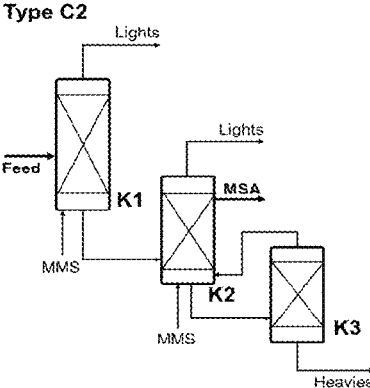

FIG. 4 shows a distillation set up with three functional distillation columns.

Figure 5:
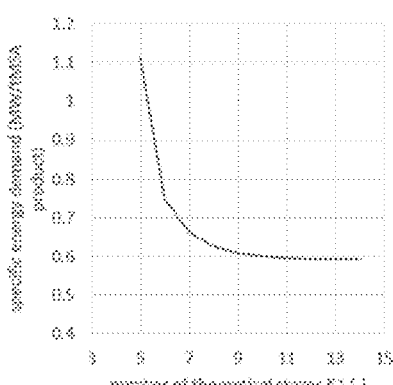
Figure 5:
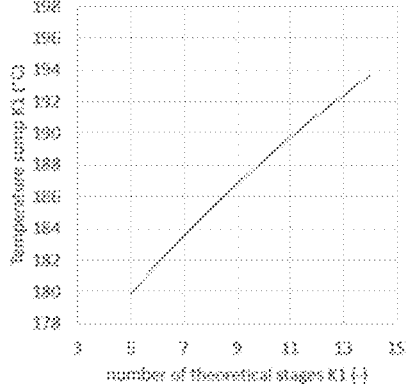

FIG. 5 illustrates the trade-off between reduction of the specific energy demand and temperature increase in the sump/reboiler for varying number of theoretical stages of K1, as discussed in Example 1.

Figure 6:
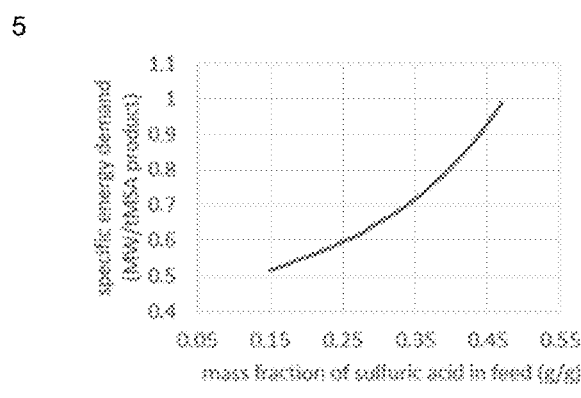
Figure 6:
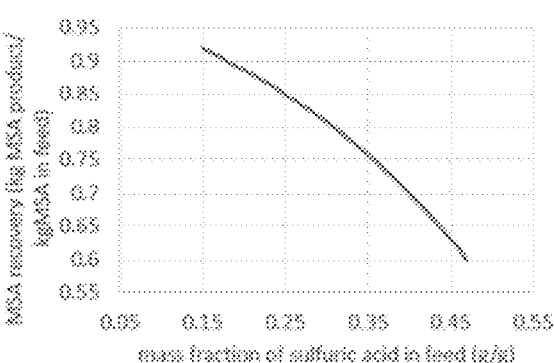

FIG. 6 shows the impact of a variation in the sulfuric acid concentration in the feed on the specific energy demand, and recovery rate of MSA, as discussed in Example 2.

Figure 7:
Figure 7:
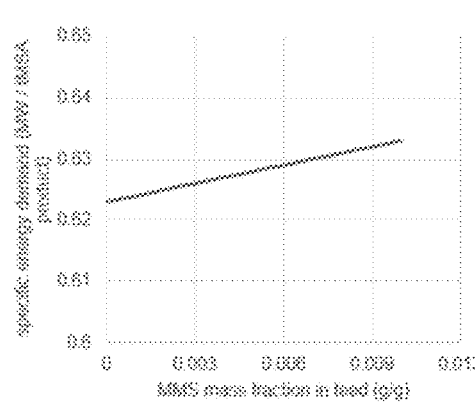

FIG. 7 shows the impact of a variation in the sulfuric acid concentration in the feed on mass fraction, as discussed in Example 2.

Figure 8:
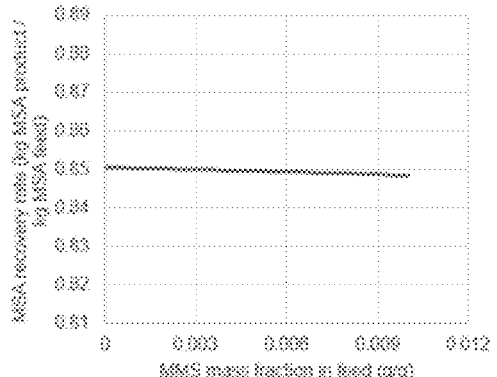

FIG. 8 shows the impact of a variation in the sulfuric acid concentration in the feed on the specific energy demand, and recovery rate of MSA with MMS-concentration in the feed, as discussed in Example 3.

EXAMPLES

The examples were carried out under the condition that the below product specifications are met:
a) Specifications of MSA-product stream:
MSA purity>=99.9% wt. MSA
$H_2SO_4$=<20 ppm (wt.)
$H_2O$=<50 ppm or 30 ppm (wt.)
MMS=<100 ppm or 20 ppm (wt.)
b) Specifications of the reactor recycle: equal to 30% wt. MSA in the $H_2SO_4$ recycle stream.

In cases, where the target specification is not achieved, the results are marked with a star symbol (*) (see Table 2).

It will be easily understood for the person skilled in the art that the set-up also can handle product specifications with higher amounts of side products. While the general set-up of the system will not change, namely three columns with MSA leaving the system via bottom outlet, especially the energy demand and yield may vary when the stream to the distillation displays different compositions and and/or in case other specifications than above for MSA are targeted. The necessary fine-tuning of operating conditions will be easy to do for a person skilled in the art.

All examples are based on the following process parameters:
a) Capacity: product stream mass flow of 2000 kg/h
b) Feed preheating by a temperature of 120° C.
c) Reactions: Due to thermal degradation of MSA, MMS and other decomposition products may form in the columns.

To evaluate and compare the results the following performance indicators were chosen:
MSA product specification
Specific energy demand (reboiler duty in MW/t MSA product)
MSA recovery rate in kg/kg. Here, the MSA recovery rate is defined as the fraction of MSA product mass flow to the MSA mass flow in the fresh feed.

$$\text{recovery rate} = \frac{\dot{m}_{MSA,product}}{\dot{m}_{MSA,feed}} \quad \text{Eq. 1}$$

MMS formation in kg/h due to thermal degradation.
The feeds used in the below examples are obtainable in the processes described above e.g. in WO 2015/071455, Kappenthuler et al. [*Journal of Cleaner Production*, 202, 2018] or in EP Appl. No. 19190499.4.

Comparative Example 1: Performance of designs with up to two functional distillation columns and purified MSA being delivered as liquid side-draw of the first column. The distillation setups considered for this example are shown in FIG. 3. The composition of the feed to the MSA-purification section is given in Table 1.

TABLE 1

| Composition of the feed to the MSA-purification section | |
| --- | --- |
| Component | Mass fraction (wt.-%) |
| $SO_3$ | 0% |
| $H_2O$ | 1.0% |
| MBS | 0.3% |
| MMS | 0.4% |
| MSAA | 0% |
| MSA | 73% |
| MDSA | 0.3% |
| $H_2SO_4$ | 25% |

The purified MSA product stream was leaving K1 as liquid side-discharge above the feed stage of column K1. Water and light boiling side-products of the reaction (e.g. MBS, MMS) were separated from MSA in K1 and left the column at the top. Sulfuric acid was delivered as bottoms stream of K1 in a mixture with MSA and high boiling side-products of the reaction (e.g. MDSA). To reduce losses of MSA product, the sulfuric acid-rich stream which is meant to be recycled to the reactor, was conditioned to 30 wt.-% MSA.

Due to the pressure loss over the column, the MSA target specification given above cannot be reached in a single column (Type C1-1). For this reason, the bottoms stream of K1 (with an MSA content higher than 30 wt.-%) was directed to a subsequent distillation column K2 (Design C1-2) or a cascade of evaporators W2-N (Design C1-3), where the stream was enriched further with sulfuric acid. The MSA-rich stream from the top of K2 or from W2 was returned to K1. The sulfuric acid-rich stream ("heavies") was leaving the set-up at the bottom of K2 or of W2 with 30 wt.-% MSA.

However, for all distillation designs of Type C1 with the MSA-product delivery as a liquid side-discharge above the feed stage and the formation of thermal degradation products like MMS, the product specification regarding MMS were not achieved (Table 2). In addition, the specific energy demand was higher than in the inventive examples 1 to 4.

Compared to WO2018/219726, which discloses distillation set-ups of Type C1, the composition of the feed summarized in Table 1 was more complex with a higher amount of side product. This comparative example showed, that with a complex feed composition a robust and economic separation of light boilers from MSA is not possible with a liquid side discharge and up to two columns.

Even for low concentration of sulfuric acid in the feed (e.g. 15 wt.-%) the MMS concentration in the MSA purified stream was above the specified limit of 100 ppm-wt. A variation of the sulfuric acid concentration in the feed from 15 to 47%-wt showed concentrations of MMS in the purified MSA stream from 104 to 120 ppm-wt and concentrations of water for 72 to 90 ppm-wt. The required specific energy demand for 15 wt.-% sulfuric acid in feed was 1.2 MW/tMSA product, while for 47%-wt sulfuric acid in the feed, the required energy demand was much higher, equal to 2.6 MW/tMSA product.

The light boiling components were separated from the main MSA stream in a first distillation column K1. In the second distillation column K2 the rest of the light components were separated from the MSA stream from the top of the column. The MSA product stream was a liquid side-

TABLE 2

Key parameters and performance of a distillation set-up
with up to two columns and a liquid side discharge

| | Design C1-1 | |
|---|---|---|
| Separation set-up | One distillation column (K1) for both product recovery and conditioning of the reactor recycle. MSA-product as liquid side-draw of K1 above feed stage. | |
| Theoretical stages | 8 | 9 |
| Pressure (mbar) | 7 for K1 | 7 for K1 |
| Performance | | |
| Product quality | 99.96 wt.-% MSA 20 ppm wt. $H_2SO_4$ 110 ppm wt. $H_2O$ * 228 ppm wt. MMS * | 99.96 wt.-% MSA 20 ppm wt. $H_2SO_4$ 126 ppm wt. $H_2O$ * 180 ppm wt. MMS * |
| MSA-concentration in bottom stream | MSA: 54.1 wt.-% * | MSA: 30 wt.-% * |
| Bottom Temperature | $T_{sump}$ K1: 185° C. | $T_{sump}$ K1: 195° C.* |
| F-Factor | F-Factor = 2.0 | F-Factor = 1.9 |
| MMS formation (kg/h) | 18.3 | 26.8 |
| Specific energy demand (MW/tMSA Product) | 1.110 | 1.126 |
| MSA recovery rate (kg/kg) | 0.590 | 0.541 |

| | Design C1-2 | Design C1-3 |
|---|---|---|
| Separation set-up | First distillation column (K1) for product recovery and second distillation column (K2) for conditioning of the reactor recycle. Distillate of K2 returns to K1 bottoms. MSA-product as liquid side-draw of K1 above feed stage. | Distillation column (K1) for product recovery, followed by a cascade of two evaporators (W3-1, W3-2) for conditioning of the reactor recycle. Distillates of W3-1 and W3-2 return to K1 bottoms. MSA-product as liquid side-draw of K1 above feed stage |
| Theoretical stages | 8 for K1, 2 for K2 | 8 for K1 |
| Pressure (mbar) | 7 for K1, 8 for K2 | 7 for K1, 6 for W3-1, W3-2 |
| Performance | | |
| Product quality | 99.98 wt.-% MSA 20 ppm wt. $H_2SO_4$ 75 ppm wt. $H_2O$ 118 ppm wt. MMS * | 99.97 wt.-% MSA 20 ppm wt. $H_2SO_4$ 97 ppm wt. $H_2O$ 113 ppm wt. MMS * |
| MSA-concentration in bottom stream | MSA 30 wt.-% | MSA 30 wt.-% |
| Bottom Temperature | $T_{sump}$ K1: 185° C., $T_{sump}$ K2: 183° C. | $T_{sump}$ K1 182° C.; $T_{out}$ W3-1: 171° C.; $T_{out}$ W3-2: 175° C.; |
| F-Factor | F-Factor K1 = 2.0 F-Factor K2 = 1.0 | F-Factor K1 = 2.0 |
| MMS formation (kg/h) | 23.2 | 11.5 |
| Specific energy demand (MW/tMSA Product) | 1.301 | 1.333 |
| MSA recovery rate (kg/kg) | 0.768 | 0.820 |

Comparative Example 2: Performance of a design with three functional distillation columns, where the MSA product was delivered as liquid side-discharge of the second column, for an MSA-rich feed. This distillation set-up is depicted in FIG. 4. The feed had the same composition as in Comparative Example 1.

discharge from K2 above feed stage. The remaining MSA and sulfuric acid at the bottom of K2 were fed to distillation column K3. A MSA-rich stream was generated at the top of K3 and returned to the bottoms of K2. The heavies left the distillation set-up at the bottoms discharge of K3.

For this design all specifications for the product stream and the sulfuric acid recycle could be achieved (Table 3).

Also a high product recovery rate could be reached, however, the specific energy demand was still too high.

TABLE 3

Key parameters and performance of a distillation set-up with three distillation columns and a liquid side discharge

| | Design C2 |
|---|---|
| Separation set-up | First distillation column (K1) for separation of light boiling components, second distillation column (K2) for product recovery and third distillation column (K3) for conditioning of the reactor recycle. Distillate of K3 returns to K2 bottoms. MSA-product as side-draw of K2 above feed stage. |
| Theoretical stages | 7 for K1, 9 for K2, 3 for K3 |
| Pressure (mbar) | 9 for K1, 8 for K2, 7 for K3 |
| Product quality | 99.99 wt.-% MSA<br>20 ppm wt. $H_2SO_4$<br>1 ppb wt. $H_2O$<br>100 ppm wt. MMS |
| MSA Concentration Bottom stream | MSA 30 wt.-% |
| Bottom Temperature | $T_{sump}$ K1 181° C.<br>$T_{sump}$ K2 185° C.<br>$T_{sump}$ K3 183° C. |
| F-Factor | F-factor K1 = 0.9<br>F-factor K2 = 1.2<br>F-factor K3 = 1.7 |
| MMS formation (kg/h) | 15.1 |

TABLE 3-continued

Key parameters and performance of a distillation set-up with three distillation columns and a liquid side discharge

| | Design C2 |
|---|---|
| Specific energy demand (MW/ tMSA Product) | 0.853 |
| MSA recovery rate (kg/kg) | 0.820 |

Example 1: Performance of the proposed design Type 1 according to the present invention for MSA-rich feed as shown in FIG. 2. The feed had the same composition as in Comparative Example 1 (see Table 1).

Sulfuric acid and heavy boiling side-products of the reaction were separated from the main MSA stream in a first distillation column K1. In the second distillation column K2 remaining light components were separated from the MSA stream. The MSA product stream was delivered as bottoms liquid discharge of K2. The remaining MSA and sulfuric acid from column K1 were fed to distillation column K3 (Design 1-1) or to a cascade of evaporators (Design 1-2). A MSA-rich stream was delivered from the top of K3 and returned to the bottoms of K1. The bottoms discharge of K3 left the distillation system.

All specifications for the product stream and the sulfuric acid recycle were fulfilled. Compared to the distillation design of type C1 and C2 a high product recovery rate could be achieved with a significant reduction of the specific energy demand.

TABLE 4

Key parameters and performance of the distillation set-up according to the present invention (Design 1)

| | Design 1-1 | Design 1-2 |
|---|---|---|
| Separation set-up | First distillation column (K1) for separation of heavy boiling components, second distillation column (K2) for product recovery and third distillation column (K3) for conditioning of the reactor recycle. Distillate of K3 returns to K1 bottoms. MSA-product as liquid or gaseous bottoms residue of K2. | First distillation column (K1) for separation of heavy boiling components, second distillation column (K2) for product recovery and a cascade of two evaporators (W3-1, W3-2) for conditioning of the reactor recycle. MSA-rich condensate of W3-1 returns to K1 bottoms and of W3-2 returns to W3-1. MSA-product as liquid or gaseous bottoms residue of K2. |
| Theoretical stages | 8 for K1, 4 for K2, 3 for K3 | 8 for K1, 4 for K2 |
| Pressure (mbar) | 7 for K1, 10 for K2, 7 for K3 | 7 for K1, 10 for K2, 7 for W3-1, 7 for W3-2 |
| Product quality | 99.98% wt. MSA<br>20 ppm wt. $H_2SO_4$<br>33 ppm wt. $H_2O$<br>100 ppm wt. MMS | 99.98% wt. MSA<br>20 ppm wt. $H_2SO_4$<br>38 ppm wt. $H_2O$<br>100 ppm wt. MMS |
| MSA Concentration Bottom stream | MSA 30% wt. | MSA 30% wt. |
| Bottom Temperature | $T_{sump}$ K1 185° C.<br>$T_{sump}$ K2 169° C.<br>$T_{sump}$ K3 186° C. | $T_{sump}$ K1 184° C.<br>$T_{sump}$ K2 169° C.<br>T W3-1 172° C.<br>T W3-2 175° C. |
| F-Factor | F-factor K1 = 1.6<br>F-factor K2 = 0.5<br>F-factor K3 = 2.0 | F-factor K1 = 1.5<br>F-factor K2 = 0.5 |
| MMS formation (kg/h) | 10.7 | 7.6 |

TABLE 4-continued

Key parameters and performance of the distillation set-up
according to the present invention (Design 1)

|  | Design 1-1 | Design 1-2 |
|---|---|---|
| Specific energy demand (MW/ tMSA Product) | 0.627 | 0.767 |
| MSA recovery rate (kg/kg) | 0.850 | 0.851 |

The choice of the number of theoretical stages for K1 (and therefore the height of the packing) was a trade-off between the reduction of specific energy demand and requirements on the thermal stability of the equipment material. On the one hand, higher number of stages results to lower energy demand for column K1. On the other hand, a higher number of stages corresponds to higher pressure drop along the packing and therefore higher temperature in the sump and the reboiler of K1, having the disadvantage of higher MMS formation. Thereafter, the thermal stability of equipment material defines the maximum operating temperature allowed for the reboiler and the maximum number of the theoretical stages for K1.

FIG. 5 illustrates the trade-off between reduction of the specific energy demand and temperature increase in the sump/reboiler for varying number of theoretical stages of K1. The specific energy demand for Design 1-1 could be further reduced to 0.593 MW/tMSA product, if temperatures of up to 194° C. were allowed in the sump of K1. For all cases shown in FIG. 5, the product specifications were achieved, namely with mass fraction of sulfuric acid by 20 ppm, mass fraction of MMS by 100 ppm and mass fraction of water varying between 30 and 36 ppm.

The energy demand of the designs of type 1 is approximately 26% lower than the energy demand of designs of type C2 and of approximately 52% lower than the energy demand by the designs of type C1, which were both given above in the comparative examples.

Example 2: In example 2 the operation of the same distillation design as in Example 1 was used, except with a higher $H_2SO_4$-concentration in the feed. Thus, the $H_2SO_4$-concentration was varied between 15 and 47 wt.-%. Proposed design according to the present invention operated with a sulfuric-acid rich feed and variation of feed composition regarding sulfuric acid.

TABLE 5

Composition of sulfuric-acid rich feed
to the MSA-purification section

| Component | Mass fraction (wt. %) |
|---|---|
| $SO_3$ | 0% |
| $H_2O$ | 1.0% |
| MBS | 0.3% |
| MMS | 0.4% |
| MSAA | 0% |
| MSA | 53% |
| MDSA | 0.3% |
| $H_2SO_4$ | 45 |

In this example, Design 1-1 was used with sulfuric acid concentration in the feed from 15 to 45 wt.-%. With the designs of type 1 the product specifications could be achieved. FIG. 6 and FIG. 7 show the impact of a variation in the sulfuric acid concentration in the feed on the specific energy demand, the recovery rate of MSA and the product specifications. The energy demand for a concentration of 45 wt.-% sulfuric acid in the feed was approximately 50% higher than for a concentration of 25 wt.-% sulfuric acid in the feed. To obtain a constant production rate of MSA a higher feed rate was used and the reboiler duty was increased. Although with higher sulfuric acid concentrations in the feed the product recovery rate was reduced, but designs of type 1 proved to be robust and the product specifications were achieved in all cases: sulfuric acid 20 ppm-wt, MMS 100 ppm-wt and water from 28 to 46 ppm-wt in the MSA product stream (FIG. 7). Comparing these findings with Eq. 1, it is obvious that the reduction of the recovery rate, was also caused by a dilution of the feed. The current inventive example also showed, that a high MSA concentration in the feed to the distillation was beneficial.

TABLE 6

Key parameters and performance of the distillation set-up according
to the present invention (Design 1) with a variation of the
sulfuric acid concentration in the feed to 47 wt.-%

|  | Design 1-1 high sulfuric acid concentration (47 wt.-%) |
|---|---|
| Separation set-up | First distillation column (K1) for separation of heavy boiling components, second distillation column (K2) for product recovery and third distillation column (K3) for conditioning of the reactor recycle. Distillate of K3 returns to K1 bottoms. MSA-product as liquid or gaseous bottoms residue of K2. |
| Theoretical stages | 8 for K1, 4 for K2, 3 for K3 |
| Pressure (mbar) | 7 for K1, 10 for K2, 7 for K3 |
| Product quality | 99.98% wt. MSA 20 ppm wt. $H_2SO_4$ 43 ppm wt. $H_2O$ 100 ppm wt. MMS |
| MSA Concentration bottom stream | MSA 30 wt.-% |
| Bottom Temperature | $T_{sump}$ K1 189° C. $T_{sump}$ K2 169° C. $T_{sump}$ K3 186° C. |
| F-Factor | F-factor K1 = 2.0 F-factor K2 = 0.6 F-factor K3 = 2.0 |
| MMS formation (kg/h) | 19.6 |
| Specific energy demand (MW/ tMSA Product) | 0.991 |
| MSA recovery rate (kg/kg) | 0.600 |

Example 3: Example 3 shows the performance of the proposed design with a variation of the MMS-concentration in the feed.

TABLE 7

Composition of feed to the MSA-purification section
for variation of the MMS concentration

| Component | Mass fraction (wt. %) |
|-----------|----------------------|
| $SO_3$ | 0% |
| $H_2O$ | 0.01% |
| MBS | 0.3% |
| MMS | 0 to 1% |
| MSAA | 0% |
| MSA | 73.4 to 72.4% |
| MDSA | 0.3% |
| $H_2SO_4$ | 25% |

The same design of type 1-1, which is shown in FIG. 2 was used in this example and the MMS-concentration in the feed was varied from 0 to 1 wt.-%. It was found that the design according to this invention was robust towards variation of the MMS content in the feed. The separation task and the product specifications were fulfilled over the whole concentration range (Table 8). Furthermore, the specific energy demand and the MSA recovery rate were only slightly changed with the concentration of MMS (FIG. 8).

TABLE 8

Key parameters and performance of the distillation set-up
according to the present invention (Design 1) with a
variation of the MMS-concentration in the feed.

| | Design 1-1 Variation MMS-concentration |
|---|---|
| Separation set-up | First distillation column (K1) for separation of heavy boiling components, second distillation column (K2) for product recovery and third distillation column (K3) for conditioning of the reactor recycle. Distillate of K3 returns to K1 bottoms. MSA-product as liquid or gaseous bottoms residue of K2. |
| Theoretical stages | 8 for K1, 4 for K2, 3 for K3 |
| Pressure (mbar) | 7 for K1, 10 for K2, 7 for K3 |
| Product quality | 99.98 wt.-% MSA 20 ppm wt. $H_2SO_4$ 35 ppm wt. $H_2O$ 100 ppm wt. MMS |
| MSA Concentration bottom stream | MSA 30 wt.-%. |
| Bottom Temperature | $T_{sump}$ K1 185° C. $T_{sump}$ K2 169° C. $T_{sump}$ K3 186° C. |
| F-Factor | F-factor K1 = 1.6 F-factor K2 = 0.5 to 0.6 F-factor K3 = 2.0 |
| MMS formation (kg/h) | 10.7 |
| Specific energy demand (MW/ tMSA Product) | 0.622 to 0.633 |
| MSA recovery rate (kg/kg) | 0.851 to 0.849 |

Example 4: Performance of the proposed design 1-1 according to the present invention (FIG. 2) for a water-free feed with small amounts of $SO_3$.

TABLE 9

Composition of water-free feed to the MSA-purification
section with small amounts of $SO_3$.

| Component | Mass fraction (wt. %) |
|-----------|----------------------|
| $SO_3$ | 0.04% |
| $H_2O$ | 0% |

TABLE 9-continued

Composition of water-free feed to the MSA-purification
section with small amounts of $SO_3$.

| Component | Mass fraction (wt. %) |
|-----------|----------------------|
| MBS | 0.3% |
| MMS | 0.4% |
| MSAA | 0% |
| MSA | 73% |
| MDSA | 0.3% |
| $H_2SO_4$ | 25.96% |

Figure 1:
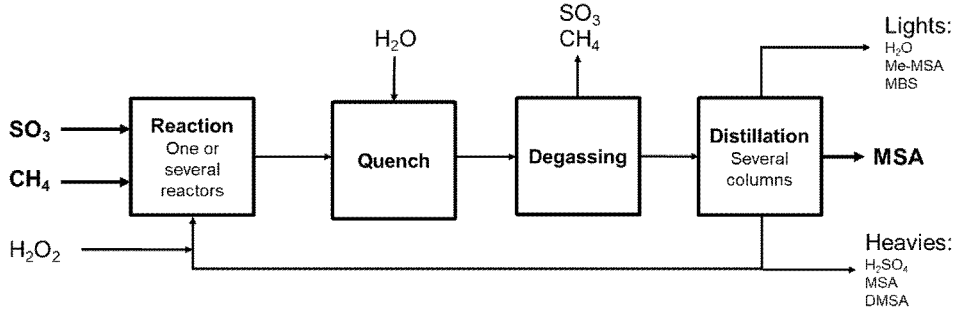
FIG. 1 shows a process for the production and purification of methane sulfonic acid.

In this example the feed comprised $SO_3$ (assuming in the quenching step of FIG. 1 not all $SO_3$ is completely converted with water to sulfuric acid). As sulfur trioxide has the highest vapor pressure of all components, it exited the system with the off-gas of distillation column K1. Consequently, the product specifications could be achieved too (Table 10). The product recovery rate was maintained, and design 1 proved to be robust as the separation task was achieved with the same energy demand.

TABLE 10

Key parameters and performance of the distillation
set-up according to the present invention (Design
1) with a water-free feed containing $SO_3$

| | Design 1-1 - Water-free feed containing $SO_3$ |
|---|---|
| Separation set-up | First distillation column (K1) for separation of heavy boiling components, second distillation column (K2) for product recovery and third distillation column (K3) for conditioning of the reactor recycle. Distillate of K3 returns to K1 bottoms. MSA-product as liquid or gaseous bottoms residue of K2. |
| Theoretical stages | 8 for K1, 4 for K2, 3 for K3 |
| Pressure (mbar) | 7 for K1, 10 for K2, 7 for K3 |
| Product quality | 99.98 wt.-% MSA 20 ppm wt. $H_2SO_4$ 100 ppm wt. MMS |
| MSA Concentration bottom stream | MSA 30 wt.-% |
| Bottom Temperature | $T_{sump}$ K1 182° C. $T_{sump}$ K2 169° C. $T_{sump}$ K3 186° C. |
| F-Factor | F-factor K1 = 1.5 F-factor K2 = 0.5 F-factor K3 = 2.0 |
| MMS formation (kg/h) | 10.7 |
| Specific energy demand (MW/ tMSA Product) | 0.625 |
| MSA recovery rate (kg/kg) | 0.845 |

As a result, the inventive process leads to a reduction of the energy demand of up to 52%, compared to the designs where MSA product is delivered as a liquid side-discharge above the feed stage (comparative examples 1 and 2). For high side-product concentrations in feed and for a higher MMS formation due to thermal degradation of MSA at a larger hold-up and a residence time higher than 2 hours, designs with up to two functional distillation columns do not guarantee that the product specifications regarding MMS target spec can be achieved (Comparative Example 1). The inventive process is robust against variation of the feed composition, i.e. higher $H_2SO_4$ mass fraction (up to 47%) (Example 2) and higher concentrations of reaction side-products like MMS (Example 3). Moreover, it was shown, that lower mass fractions of sulfuric acid in the feed were beneficial as the energy demand for the process could be reduced. A high mass fraction of sulfuric acid and/or MMS in the feed to the distillation led to an increase in the specific energy demand and a reduction of the MSA recovery rate. With the invention on hand the formation of thermal degradation products, like MMS, could be limited by keeping the temperature in the bottoms of columns below 185° C. As shown in the examples all product specifications were achieved with this boundary condition. If the temperature in the bottom of the columns was higher, more side products were formed. As discussed above, the inventive process guarantees a stable operation even with higher amounts of side-products. Additionally, the residence time in bottom of the distillation columns could be limited to reduce the formation rate of degradation products, e.g. by reducing the inner diameter of sump of each column compared to the rest of the column.

Finally, a further object of the present invention is also the use of MSA, obtainable by the inventive process, for cleaning applications, for chemical synthesis or in an electroplating process.

The invention claimed is:

1. A process for separating anhydrous methanesulfonic acid from a reaction mixture comprising methanesulfonic acid and sulfuric acid by distillation, comprising feeding the reaction mixture into a first column K1 and producing a top stream of column K1 and a bottom stream of column K1, transferring the top stream of column K1 to a second column K2, in which purified anhydrous methanesulfonic acid is obtained from a bottom stream of column K2, and transferring the bottom stream of column K1 to either a third column K3 or an evaporator W3-1, in which a top stream of column K3 or a top stream of evaporator W3-1 is recycled back into column K1, and in which a bottom stream of column K3 or a bottom stream of evaporator W3-1 is separated from the distillation process.

2. The process according to claim 1, wherein, in addition to evaporator W3-1, further (n–1) evaporators W3-2, W3-3, . . . , W3-n, n being an integer from 2 to 10, are used, wherein a bottom stream of each evaporator W3-k, k being an integer from 1 to (n–1)) is transferred to each evaporator W3-(k+1), and wherein a top stream of each evaporator W3-(k+1) is transferred back to each evaporator W3-k, while a bottom stream of evaporator W3-n is separated from the distillation process.

3. The process according to claim 1, wherein the reaction mixture comprises 55 to 95 wt. % methanesulfonic acid, 5 to 45 wt. % sulfuric acid, 0 to 5 wt. % methanesulfonic acid anhydride, 0 to 1 wt. % side products, 0 to 5% $SO_3$, 0 to 5 wt. % of water and traces of methane, wherein the sum of all components sums up to 100 wt. %, and wherein the side products comprise methylmethanesulfonate and/or methylbisulfate and/or methanedisulfonic acid, and wherein the amount of components other than methanesulfonic acid and sulfuric acid is in the range of 0 to 10 wt. %.

4. The process according to claim 1, wherein columns K1, K2 and optionally K3 are provided within a single column.

5. The process according to claim 1, wherein the bottom residue of column K3 or evaporator or cascade of evaporators W3-n contains at least 60 wt. % of sulfuric acid.

6. The process according to claim 1, wherein the pressure at the head of the columns and optionally evaporators ranges from 0.1 to 50 mbar, for all distillation columns K1, K2 and optionally K3 and evaporators W3-n.

7. The process according to claim 1, wherein the temperature at the bottom of the columns and optionally evaporators ranges from 140 to 220° C., in all distillation columns K1, K2 and optionally K3 and evaporators W3-n.

8. The process according to claim 1, wherein purified MSA leaves the distillation at bottom of K2 with a specification of <500 ppm sulfuric acid, <1000 ppm MMS, 0.5 wt. % water.

9. The process according to claim 1, wherein MSA leaves the distillation with a purity of at least 98 wt %.

10. The process according to claim 1, wherein the process is a batch or a continuous process.

11. The process according to claim 1, wherein the MSA recovery rate in the distillation is at least 80%.

12. The process according to claim 1, wherein at least a part of the bottom fraction of the MSA distillation column K3 is not purged from the system but at least partially recycled to the synthesis step of the starter solution or to the synthesis step of the MSA synthesis with methane and SO3.

13. The process according to claim 1, wherein the residence time in each distillation column and optionally evaporators W3-n is below 5h.

14. The process according to claim 1, wherein the ratio of the inner column diameter in the sump and the inner column diameter of the column directly above the sump for each column is in the range from 0.20 to 0.99.

15. The process according to claim 1, wherein columns K1, K2 and optionally K3 are provided in parallel.

* * * * *